United States Patent [19]

Ishizue et al.

[11] Patent Number: 5,445,830
[45] Date of Patent: Aug. 29, 1995

[54] HIGHLY ABSORBABLE PHARMACEUTICAL COMPOSITION

[75] Inventors: Yoshihiro Ishizue; Kozo Ishida; Masaaki Odomi; Toru Nishibayashi; Kaszuyo Koshino, all of Tokushima, Japan

[73] Assignee: Otsuka Pharmaceutical Co., Ltd., Tokyo, Japan

[21] Appl. No.: 17,443

[22] Filed: Feb. 12, 1993

Related U.S. Application Data

[63] Continuation of Ser. No. 742,432, Aug. 8, 1991, abandoned, which is a continuation-in-part of Ser. No. 554,875, Jul. 20, 1990, abandoned.

[30] Foreign Application Priority Data

Jul. 25, 1989 [JP] Japan ................................. 1-192413

[51] Int. Cl.⁶ .............................................. A61K 9/14
[52] U.S. Cl. ...................................... 424/484; 424/489
[58] Field of Search ................................. 424/484, 489

[56] References Cited

U.S. PATENT DOCUMENTS

4,547,359 10/1985 Zierenberg et al. .................. 424/19
4,923,977 5/1990 Lang ....................................... 424/45
4,940,556 7/1990 MacFarlane et al. ............... 424/501
4,971,790 11/1990 Magruder ............................ 424/435

FOREIGN PATENT DOCUMENTS

0145434 3/1984 European Pat. Off. .
61-227524 9/1986 Japan .

OTHER PUBLICATIONS

Derwent Abstract No. 84-264656/43 (relating to USP 4,547,359), Derwent Publications Ltd.

Primary Examiner—Thurman K. Page
Assistant Examiner—W. Benston
Attorney, Agent, or Firm—Finnegan, Henderson, Farabow, Garrett & Dunner

[57] ABSTRACT

A highly absorbable pharmaceutical composition containing, as the active ingredient, methyl 3-phenyl-2(E)-propenyl 1,4-dihydro-2,6-dimethyl-4-(3-nitrophenyl)-pyridine-3,5-dicarboxylate in an amorphous state and a pH-dependent type copolymer of methacrylic acid or its derivatives which composition has been prepared by dissolving the two components together in an organic solvent and thereafter removing the solvent.

6 Claims, 3 Drawing Sheets

//www.w3.org/1999/xhtml">
HIGHLY ABSORBABLE PHARMACEUTICAL COMPOSITION

This application is a continuation, of application Ser. No. 07/742,432, filed Aug. 8, 1991, now abandoned, which is a continuation-in-part of application Ser. No. 07/554,875, filed Jul. 20, 1990, now abandoned.

FIELD OF THE INVENTION

The present invention relates to a highly absorbable pharmaceutical composition.

BACKGROUND OF THE INVENTION

Methyl 3-phenyl-2(E)-propenyl 1,4-dihydro2,6-dimethyl-4-(3-nitrophenyl)pyridine-3,5-dicarboxylate (hereinafter referred to as the "compound") has effective pharmacological activities for example antihypertensive effect and others, which have been developed by the present inventors [Japanese Patent Kokai (Laid-open) No. 60-120861 (1985), and European Patent Publication No. 0,145,434 (June 19, 1985)]. However, the compound is practically insoluble in an aqueous solution (0.5 μg/ml), and has quite a low absorbability rate through the gastrointestinal tract when it is administered orally.

The present inventors have made an extensive study to improve the solubility of the compound in an aqueous solution, so as to make it possible to sustain a supersaturated state thereof for a long period of time, and to improve the absorbability thereof through the gastrointestinal tract. During the course of study, the present inventors tried to improve the solubility thereof in an aqueous solution by making it in an amorphous state with various types of polymers. However, using polymers such as a cellulose-type high molecular compound or a polyvinylpyrrolidone or the like, the solubility of the compound was not improved. Accordingly, the present inventors continued the study and finally found that the object of the present invention can be achieved only if the compound is made in the amorphous state using pH-dependent type copolymers of methacrylic acid and its derivatives.

SUMMARY OF THE INVENTION

The present invention provides a highly absorbable pharmaceutical composition comprising in an amorphous state methyl 3-phenyl-2(E)-propenyl 1,4-dihydro-2,6-dimethyl-4-(3-nitrophenyl)-pyridine-3,5-dicarboxylate and pH-dependent type methacrylic acid copolymers.

DETAILED EXPLANATION OF THE INVENTION

Figure 1:
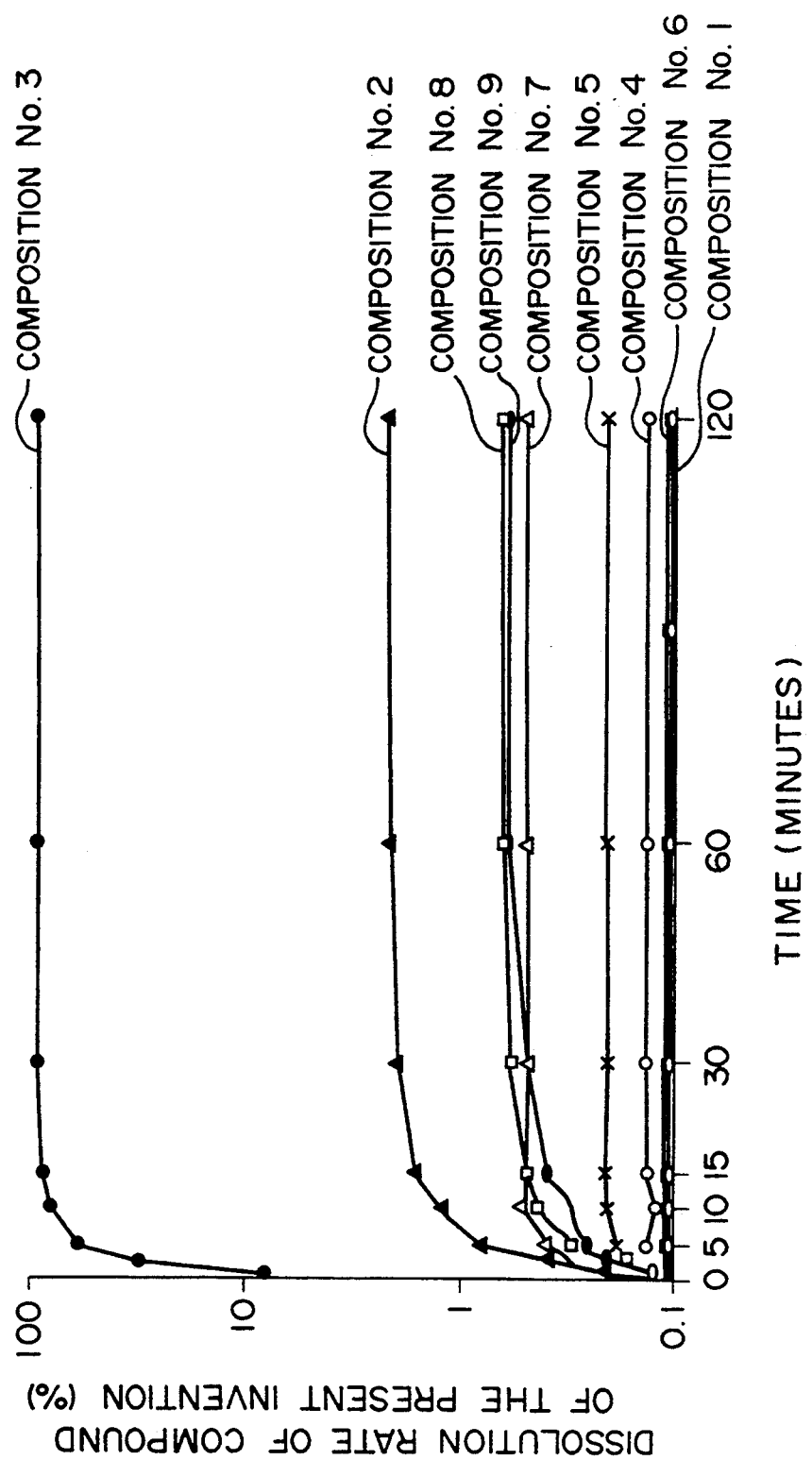
FIG. 1 and FIG. 2 show curves indicating the time-sequential changes of the dissolution rate (%) of compound dissolved from various compositions of the present invention.

As to the pH-dependent type copolymers of methacrylic acid and its derivatives, various methacrylic acid copolymers and copolymers of its derivatives which are widely known in the art can be employed so long as they are pH-dependent. Examples include trimethylammonium salts of copolymers of acrylic acid and methacrylic acid; copolymers of methacrylic acid and methyl acrylate; copolymers of methacrylic acid and methyl methacrylate; copolymers of ethyl acrylate and methyl methacrylate, copolymers of butyl methacrylate, dimethylaminoethyl methacrylate and methyl methacrylate; and the like. More specifically, Eudragit L, Eudragit S, Eudragit E, Eudragit L100, Eudragit S100 and Eudragit E100 (trademarks for pH-dependent type copolymers of methacrylic acid and derivatives thereof manufactured by Rohm and Pharma GmbH.) can be used.

Among these pH-dependent type copolymers of methacrylic acid and its derivatives, Eudragit E is an example of an aminoalkyl methacrylate copolymer which is soluble in gastric juice, and Eudragit L and Eudragit S are examples of methacrylic acid copolymers which are soluble in intestinal juice. In the highly absorbable pharmaceutical compositions of the present invention, the above-mentioned pH-dependent type methacrylic acid copolymers can be used alone or in combinations of two or more thereof.

As to the mixing ratio of the amount of the compound to the amount of the pH-dependent type methacrylic acid copolymers, generally from about 10 to 2,000 parts by weight, preferably from about 30 to 1,000 parts by weight, of the latter may be used to 100 parts by weight of the former.

If necessary, various kinds of additives, for example, water-soluble or water-swelling polymers, surfactants, polyethylene glycols, organic acids and the like which may usually be formulated with this type of pharmaceutical composition, can also be used in the composition of the present invention.

As to water-soluble or water-swelling polymers, examples include, hydroxypropylmethyl cellulose, hydroxypropyl cellulose, hydroxyethyl cellulose, polyvinylpyrrolidone, pH-independent methacrylic acid copolymers (e.g., Eudragit RL, Eudragit RS, etc.) and the like.

As to surfactants, non-ionic, cationic, anionic, and amphoteric surfactants can be used.

Furthermore, as to the organic acids, examples include citric acid, succinic acid, tartaric acid and the like.

The highly absorbable antihypertensive composition according to the present invention can be prepared by the methods as mentioned below. Thus the compound, the pH-dependent type copolymer of methacrylic acid or its derivatives and, additionally, if necessary, water-soluble or water-swelling polymers, surfactants, polyethylene glycols and organic acids, are all dissolved in an organic solvent, and then the organic solvent is removed by evaporation by conventional methods. Organic acids and other excipients for tablet compression may then be added to the composition, or an organic acid and other excipients for tablet compression may be added before the organic solvent is removed.

As to excipients for tablet compression, any excipients which are widely known in the art may be employed.

As to the organic solvents, any organic solvents which are widely known in the art may be employed, so long as they are able to dissolve both the compound and the pH-dependent type methacrylic acid copolymer. Examples of solvents include acetone, methanol, ethanol, isopropanol, dichloromethane, chloroform, and the like. Furthermore, if necessary, water may be added as a solvent.

As to methods for removing the organic solvents, evaporation, spray drying, fluidized bed coating, and centrifugal fluidized bed coating methods can be employed.

The composition of the present invention makes it possible to improve the solubility of the compound in an aqueous solution, so as to make it possible to keep a supersaturated state thereof in an aqueous solution for a long period of time. Further it improves the absorbability thereof through the gastrointestinal tract when the composition is administered orally.

The compound of the present invention has been developed mainly as a anti-hypertensive agent, and pharmaceutical compositions containing it as the active ingredient, which are able to sustain their pharmacological activities for long periods of time with less side-effects, have long been sought.

There has been known the fact that when the compound is dissolved in a solvent such as a polyethylene glycol or the like, and the solution is then administered orally, the absorbability of the compound is improved only to a certain extent. However, the absorbability can not suitably be controlled when such a solution-type pharmaceutical composition is administered orally, because side-effects may appear due to a rapid increase in the plasma concentration of the compound.

According to the present invention, however when the highly absorbable pharmaceutical composition is administered orally, the compound, which is the active ingredient of the composition, and which could not have easily been absorbed through the gastrointestinal tract, can be absorbed effectively. In addition, by selecting the type of polymer material, namely a pH-dependent type copolymer of methacrylic acid and its derivatives, and the ratio of the amount thereof to the amount of the compound in the composition, the side-effects, which can be caused by a rapid increase in the plasma concentration of the compound, can easily be controlled.

EXAMPLES

The present invention will be further explained by the following Examples.

Example 1

Into a fluidized bed granulating machine (FLOW COATER FL-10, manufactured by Freund Industrial Co., Ltd., Tokyo Japan), were placed 228 g of lactose and 30 g of corn starch. 300 g of a 4% -hydroxypropylmethyl cellulose aqueous solution was then added as a binding agent and the whole mixture was made into granules by charging the machine with air at a temperature of 70° C. for 30 minutes. The thus obtained granules were sieved through a sieve having a mesh size of 500 μm so the granules have the same average particle size.

Separately, 9 g of the "compound" and 27 g of the polymer used in each one of the pharmaceutical Compositions Nos. 2-8 mentioned below were dissolved completely in 648 g of a mixed solvent of methanol-methylene chloride (1:1), respectively to form a solution. Then each one of the solutions was coated by spraying it at a temperature of 60° C. for 35 minutes on the granules to make the following 8 types of pharmaceutical compositions. The coated granules of each one of the compositions was then filled into capsules, separately.

1) Pharmaceutical Composition No. 3

Eudragit L 100 (trademark for a methacrylic acid copolymer L manufactured by Rohm and Pharma GmbH) was used as the polymer in this pharmaceutical composition.

2) Pharmaceutical Composition No. 4

Eudragit E 100 (trademark for an aminoalkyl methacrylate copolymer manufactured by Rohm and Pharma GmbH) was used as the polymer in this pharmaceutical composition.

3) Pharmaceutical Composition No. 5

Eudragit RL 100 (trademark for an aminoalkyl methacrylate copolymer E manufactured by Rohm and Pharma GmbH) was used as the polymer in this pharmaceutical composition.

4) Pharmaceutical Composition No. 6

Eudragit RS 100 (trademark for an aminoalkyl methacrylate copolymer RS manufactured by Rohm and Pharma GmbH) was used as the polymer in this pharmaceutical composition.

5) Pharmaceutical Composition No. 2

Plasdone K-29 (trademark for a polyvinylpyrrolidone manufactures by GAF Chemical Corp.) was used as the polymer in this pharmaceutical composition.

6) Pharmaceutical Composition No. 7

TC-5E (trademark for a hydroxypropylmethyl cellulose manufactured by Shin-Etsu Chemical Co., Ltd.) was used as the polymer in this pharmaceutical composition.

7) Pharmaceutical Composition No. 8

HPC-L (trademark for a hydroxypropylmethyl cellulose manufactured by Nippon Soda Co., Ltd.) was used as the polymer in this pharmaceutical composition.

8) Pharmaceutical Composition No. 9

HP-55 (trademark for hydroxypropylmethyl cellulose phthalate manufactured by Shin-Etsu Chemical Co., Ltd.) was used as the polymer in this pharmaceutical composition.

Pharmaceutical Composition No. 1 (Reference Composition)

Into a fluidized bed granulating machine, were placed 249 g of lactose, 30 g of corn starch and 9 g of the compound. Then using a 4%-hydroxypropylmethyl cellulose aqueous solution as a binding agent, the whole mixture was made into granules in the same manner as described above. This composition was made for comparison purposes.

Example 2

To 300 g each of Pharmaceutical Compositions Nos. 3 and 4 prepared in Example 1, were added 50 g of crystalline cellulose, 100 g of lactose, 20 g of croscarmellose sodium and 5 g of magnesium stearate as excipients for tablet compression. The whole mixture was admixed directly for 1 minute and then compressed under a pressure of 500 kg to make the pharmaceutical compositions in the form of tablets.

Example 3

200 g of Pharmaceutical Composition No. 3 and 100 g of Pharmaceutical Composition No. 4 as prepared in Example 1 were placed together in a polyethylene bag and mixed in the bag for 1 minute. Then, the mixture was mixed with excipients for tablet compression similar to those used in Example 2, and the whole mixture was compressed to make the composition in the form of tablets.

Example 4

Nine (9) grams of the compound, 9 g of Eudragit L 100 (trademark for a methacrylic acid copolymer L manufactured by Rohm and Pharma GmbH), 3 g of Plasdone K-29/32 (trademark for a polyvinylpyrrolidone manufactured by GAF Chemical Corp), 0.1 g of Tween 80 (trademark for a surfactant manufactured by Kao-Atlas Corp.) and 0.5 g of polyethylene glycol 6000 were dissolved completely in 158 g of a mixed solvent of ethanol-chloroform (1:1). Then this solution was concentrated to dryness by evaporation and the thus obtained solid mass was pulverized into a powder having a suitable particle size. To the powder was added 130 g of lactose, 60 g of crystalline cellulose and 1 g of magnesium stearate and they were admixed together for 1 minute. The whole mixture was then compressed under a pressure of 500 kg to make the mixture into tablets.

Example 5

Ninety (90) grams of the compound, 9 g of Eudragit E 100 (trademark for a pH-dependent aminoalkyl methacrylate copolymer E, manufactured by Rohm and Pharma (GmbH) and 3 g of TC-5E (trademark for a hydroxypropylmethyl cellulose, manufactured by Shin-Etsu Chemical Co., Ltd.) were dissolved completely in 898 g of a mixed solvent of ethanol-methylene chloride (1:1). Then this solution was subjected to spray-drying by charging it in air at a temperature of 70° C., for 60 minutes to make it into a powder. Then this powder was made into granules using an agitation-type fluidized bed granulating machine (MP-01), with 100 g of a 40% hydroxypropylmethyl cellulose aqueous solution, containing 2 g of citric acid and dried. Next, to these dried granules were added 1,200 g of lactose, 400 g of crystalline cellulose and 10 g of magnesium stearate. They were admixed together for 1 minute and then the whole mixture was subjected to compression to make the composition in tablet form.

Example 6

Ten (10) grams of the compound and 5 g of Eudragit L 100 (trademark for a methacrylic acid copolymer L manufactured by Rohm and Pharma GmbH) were dissolved in 125 g of a mixed solvent of methylene chloride-ethanol (75:25). Then this solution was subjected to spray-drying by charging it in air at a temperature of 70° C. for 15 minutes to make it in the form of a powder. The powder was then pulverized using a jet mill. To 15 g of [the]thus prepared powder were added 285 g of lactose, 125 g of crystalline cellulose, 7.5 g of croscaromellose sodium and 2.5 g of magnesium stearate. They were mixed together and then the composition was subjected to compression under a tabletting pressure of 400 kg. Each tablet weighed 87 mg.

Example 7

Nine (9) grams of the compound, 90 g of Eudragit L 100 (trademark for a methacrylic acid copolymer L manufactured by Rohm and Pharma GmbH), 3 g of Plasmidone K-29/32 (trademark for a polyvinylpyrrolidone manufactured by GAF Chemical Corp.), 0.1 g of Tween 80 (trademark for a surfactant manufactured by Kao-Atlas Corp.) and 0.5 g of polyethylene glycol 6000 were dissolved completely in 1,670 g of a mixed solvent of ethanol-chloroform (1:1). Then this solution was concentrated to dryness by evaporation to obtain a solid mass which was then pulverized into a powder having a suitable particle size using a moltar. To the powder were added 130 g of lactose, 60 g of crystalline cellulose and 1 g of magnesium stearate and they were mixed together for 1 minute. The pharmaceutical composition thus obtained was filled into capsules in an amount corresponding to 10 mg of the compound per capsule.

Example 8

Ninety (90) grams of the compound, 27 g of Eudragit E 100 (trademark for an aminoalkyl methacrylate copolymer E manufactured by Rohm and Pharma GmbH) and 3 g of TC-5E (trademark for a hydroxymethyl cellulose manufactured by Shin-Etus Chemical Co., Ltd.) were dissolved completely in 898 g of a mixed solvent of ethanol-methylene chloride (1:1). Then this solution was subjected to spray-drying by charging it in air at a temperature of 70° C. for 60 minutes to make it in powder form. The powder was then subjected to granulation using 100 g of a 4%-hydroxylpropylmethyl cellulose aqueous solution, containing 2g of citric acid and dried. To the thus obtained dried granules were added 1,200 g of lactose, 400 g of crystalline cellulose and 10 g of magnesium stearate. The whole mixture was admixed together for 1 minute and then the mixture was subjected to compression molding to make it in the form of tablets.

Example 9

Ninety (90) grams of the compound and 63 g of Eudragit L 100 (trademark for a methacrylic acid copolymer L manufactured by Rohm and Pharma GmbH) were dissolved completely in 1,250 g of a mixed solvent of ethanol-methylene chloride (3:7). Then this solution was subjected to spray-drying by charging it in air at a temperature of 70° C. for 90 minutes to make it into a powder. To 17 g of this powder were added 600 g of lactose, 260 g of crystalline cellulose, and 15 g of croscarmellose sodium. They were mixed thoroughly for 1 minute. 5 g of magnesium stearate was then added thereto as a lubricant and the whole mixture was subjected to compression molding under a pressure of 500 kg to make it into tablets, each weighing 87 mg.

Example 10

Ninety (90) grams of the compound and 63 g of Eudragit L 100 (trademark for a methacrylic acid copolymer L manufactured by Rohm and Pharma GmbH) were dissolved completely in 1,250 g of a mixed solvent of ethanol-methylene chloride (3:7). Then this solution was subjected to spray-drying by charging it in air at a temperature of 70° C. for 90 minutes to make it into a powder. To 34 g of this powder were added 560 g of lactose, 256 g of crystalline cellulose and 15 g of croscarmellose sodium. They were mixed thoroughly for 1 minute. 5 g of magnesium stearate was then added thereto as a lubricant and the whole mixture was subjected to compression molding under a pressure of 500 kg to make it into tablets, each weighing 87 mg.

Dissolution Test

The test was conducted by the method and apparatus Dissolution Test Method No. 2 (Paddle Method) provided in Japanese Pharmacopoeia [XIth Revised Edition (1986)]. One hundred (100) microliters each of the test solutions was sampled in a time-sequential manner (5, 10, 15, 30, 60 and 120 minutes, respectively) using a microsyringe. The amount of compound dissolved from each of the pharmaceutical compositions of the present invention tested was assayed by use of high performance liquid phase chromatography.

As to the eluants, the First Fluid (pH 1.2) and the Second Fluid (pH 6.8) provided in Japanese Pharmacopoeia (XIth Revised Edition) were used.

Nine-hundred ml of each of the test solutions (First and Second Fluids) was placed in the vessel, then the paddle was rotated at a rate of 150 rpm, under a temperature of 37.0°±0.5° C. Then, each one of the pharmaceutical compositions, containing 10 mg of compound as the test sample, was put into the vessel. The test solution was sampled in time sequential manner and the amount of compound dissolved from the test sample was detected by calculating the peak area at 245 nm by a high performance liquid phase chromatography and assayed by an absolute calibration curve method.

Figure 2:
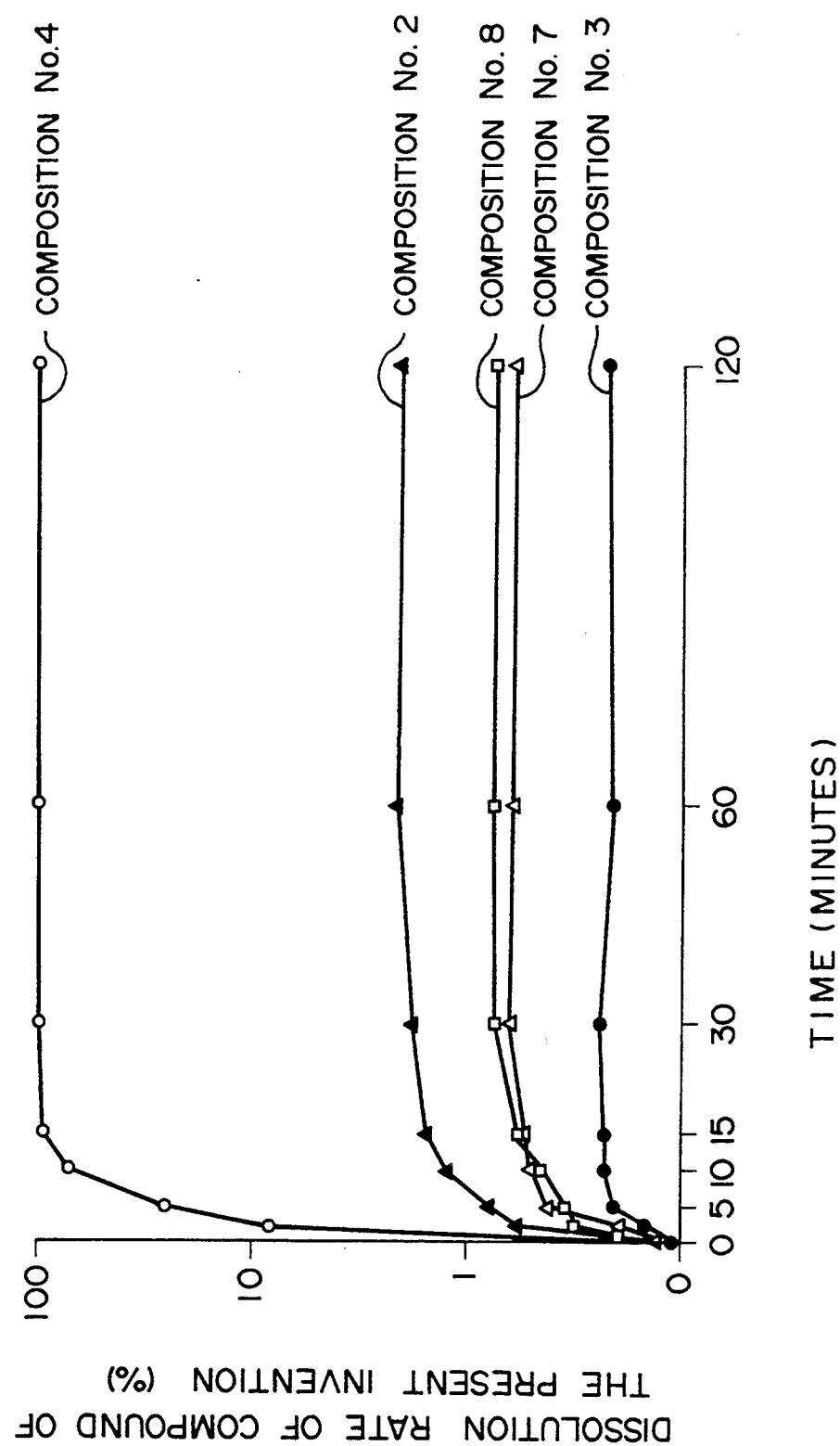

FIG. 1 plots the curves showing the time sequential changes of the dissolution rates (%) of the pharmaceutical compositions (Compositions Nos. 1–9) prepared in Example 1. The test was conducted using the Second Fluid (pH 6.8). FIG. 2 plots the curve showing the time sequential changes of the dissolution rates (%) of the pharmaceutical compositions (Compositions Nos. 2, 3, 4, 7 and 8) prepared in Example 1. The test was conducted using the First Fluid (pH 1.2).

As can be clearly seen from FIG. 1, in the test using the Second Fluid (pH 6.8), the test sample of pharmaceutical Composition No. 3, in which Eudragit L100 was used, had the highest improvement in the dissolution rate as compared with those performed by other compositions [Composition Nos. 1, 2 and 4–9]. Furthermore, Composition No. 3 is able to sustain the supersaturation state of compound of the present invention for a long period of time.

As can be seen from FIG. 2, in the test using the First Fluid (pH 1.2), the test sample of pharmaceutical Composition No. 4, in which Eudragit E100 was used, has the highest improvement in the dissolution rate as compared with those performed by other compositions (Composition Nos. 2, 3, 7 and 8).

There can be known from these test results that, the dissolution rate of the compound can be improved considerably when the compound is formulated with Eudragit E100 and the formulated composition is used in the acidic region. While, the elution rate of the compound can be improved considerably when it is formulated with Eudragit L100 and the formulated composition is used in neutral and basic regions.

Therefore, pharmaceutical compositions of the present invention can preferably be prepared by using one or both of formulating ingredients, each of which contains either one of the above-mentioned two types of polymers, respectively. Furthermore, in addition to the above-mentioned two types of polymers, other types of polymers, surfactants, polyethylene glycols, organic acids or the like may be added singly or together with the formulating ingredients. Also suitable excipients for compression molding may be added and the whole mixture made into the desired form.

The amount of compound dissolved from the pharmaceutical composition of the present invention can be controlled essentially by changing basically the ratio of the amount of Eudragit L100 or Eudragit E100 to the amount of the compound and/or by changing the tablet compression conditions.

Comparative Absorption Test (1) Test Animal

Five (5) beagle dogs (having 10 to 12 kg of body weight) were fasted overnight and were used as the test animals.

(2) Administration method

Five (5) test dogs were kept away from oral administration of test compositions for over one week. Then each one of the pharmaceutical compositions (Compositions Nos. 1-3) was administered orally to the test dog, at a dose of 30 mg of compound per dog.

(3) Sampling the blood

About 3 ml of the blood was sampled from the test dogs in time sequence (0.5, 1, 2, 3, 4, 6 and 8 hours) after the oral administration using a syringe treated with hepaline. The blood sample was centrifuged at 3,000 rpm to obtain the serum, and serum was frozen at −20° C. and stored until its use for the measurement of the concentration of the compound.

The amount of compound in the serum sample was assayed by means of a high performance liquid phase chromatography. The test results are shown in FIG. 3.

Figure 3:
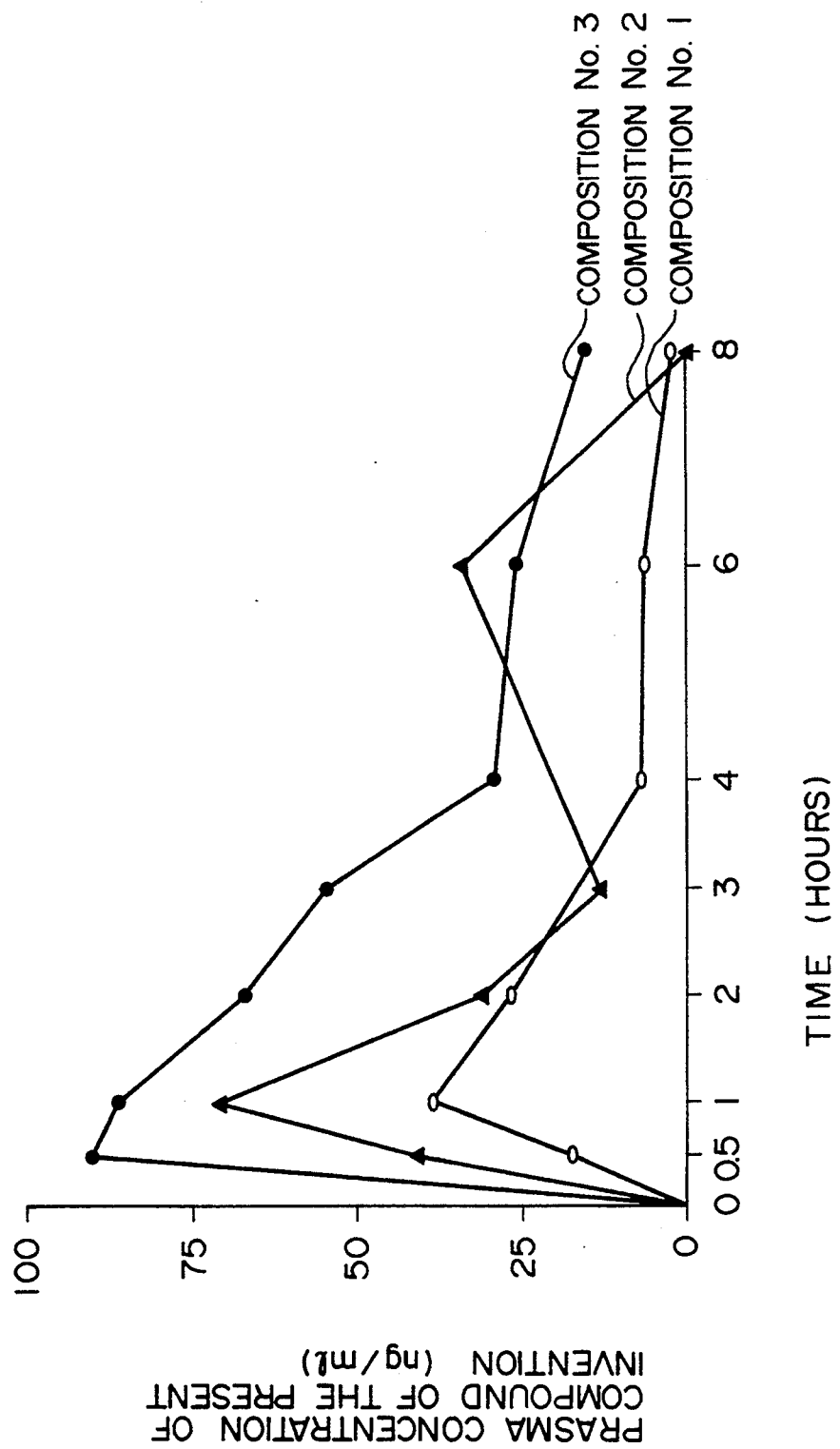
FIG. 3 shows curves indicating the time-sequential changes of plasma concentration (ng/ml) of the compound released from various compositions of the present invention, after its oral administration in beagle dogs.

As can be seen from the data in FIG. 3, the compound was rapidly increased in its plasma concentration in the pharmaceutical composition (Composition No. 3) using Eudragit L100 as the polymer, and was well absorbed from the gastrointestinal tract. It was able to keep the effective blood concentration of the compound for a long period of time, as compared with those of other compositions (Composition Nos. 1 and 2).

What is claimed is:

1. A highly absorbable pharmaceutical composition obtained by mixing together in an organic solvent, as a first component thereof, methyl 3-phenyl-2-(E)-propenyl 1,4-dihydro-2,6-dimethyl-4-(3-nitrophenyl)pyridine-3,5-dicarboxylate and, as a second component thereof, at least one pH-dependent copolymer of methacrylic acid selected from pH-dependent trimethylammonium salts of copolymers of acrylic acid and methacrylic acid; pH-dependent copolymers of methacrylic acid and methyl acrylate; pH-dependent copolymers of methacrylic acid and methyl methacrylate; pH-dependent copolymers of ethyl acrylate and methyl methacrylate; or pH-dependent copolymers of butyl methacrylate, dimethylaminoethyl methacrylate and methyl methacrylate, said organic solvent being selected from acetone, methanol, ethanol, isopropanol, methylene chloride, chloroform or mixtures thereof and being present in an amount sufficient to completely dissolve both of said first and second components, wherein the ratio of the amount of the first component to the amount of the second component is from 10 to 2,000 parts by weight of the second component per 100 parts by weight of the first component and thereafter removing the solvent to obtain said composition, the first component of the composition being present in the amorphous state.

2. The composition of claim 1, wherein the solvent is a 3:7 mixture of ethanol and methylene chloride.

3. The composition of claim 1, wherein the ratio of the amount of the first component to the amount of the second component is from 30 to 1,000 parts by weight of the second component per 100 parts by weight of the first component.

4. A process for treating hypertension in a patient suffering therefrom, which comprises administering to said patient an effective amount of the pharmaceutical composition of claim 3.

5. A process for treating hypertension in a patient suffering therefrom, which comprises administering to said patient an effective amount of the pharmaceutical composition of claim 1.

6. A process for treating hypertension in a patient suffering therefrom, which comprises administering to said patient an effective amount of the pharmaceutical composition of claim 2.

* * * * *

UNITED STATES PATENT AND TRADEMARK OFFICE
CERTIFICATE OF CORRECTION

PATENT NO. : 5,445,830
DATED : August 29, 1995
INVENTOR(S) : Yoshihiro Ishizue et al.

It is certified that error appears in the above-indentified patent and that said Letters Patent is hereby corrected as shown below:

On the title page, item [75]
INVENTORS: Front page, line 3, change "Kaszuyo" to --Kazuyo--.

Signed and Sealed this

Twenty-sixth Day of December, 1995

Attest:

BRUCE LEHMAN

Attesting Officer        Commissioner of Patents and Trademarks